(12) United States Patent
Granier et al.

(10) Patent No.: US 7,935,806 B2
(45) Date of Patent: May 3, 2011

(54) METHOD FOR PERFORMING IN VITRO DIAGNOSIS USING GENE REGULATION MECHANISMS AND CORRESPONDING DIAGNOSIS KIT

(75) Inventors: Benoit Granier, Rotheux-Rimiere (BE); Sophie Lepage, Amay (BE)

(73) Assignee: Unisensor S.A., Liege (Angleur) (BE)

( * ) Notice: Subject to any disclaimer, the term of this patent is extended or adjusted under 35 U.S.C. 154(b) by 837 days.

(21) Appl. No.: 10/496,747

(22) PCT Filed: Dec. 4, 2002

(86) PCT No.: PCT/BE02/00183
§ 371 (c)(1),
(2), (4) Date: Feb. 7, 2005

(87) PCT Pub. No.: WO03/048770
PCT Pub. Date: Jun. 12, 2003

(65) Prior Publication Data
US 2005/0130152 A1 Jun. 16, 2005

(30) Foreign Application Priority Data
Dec. 6, 2001 (EP) .................................... 01870273

(51) Int. Cl.
*C07H 21/04* (2006.01)
(52) U.S. Cl. ...................... 536/24.1; 435/320.1; 530/350
(58) Field of Classification Search ........................ None
See application file for complete search history.

(56) References Cited

U.S. PATENT DOCUMENTS

| | | | |
|---|---|---|---|
| 5,217,867 A * | 6/1993 | Evans et al. | ..................... 435/7.1 |
| 5,854,010 A | 12/1998 | Denison et al. | |
| 6,025,192 A * | 2/2000 | Beach et al. | ..................... 506/14 |
| 6,133,027 A | 10/2000 | Yee et al. | |

OTHER PUBLICATIONS

O'Gorman et al., The Journal of Biological Chemistry, vol. 252, 1977, pp. 3565-3571.*
Lederer et al., Biochemistry, vol. 35, 1996, pp. 7439-7446.*
Pook et al. "Affinities of mABs to Tet repressor complexed with operator or tetracycline suggest conformational changes associated with induction." Eur. J. of Biochem. 258, 915-922 (1998).
Kurittu, J. et al. "Qualitative detection of tetracycline residues in milk with a luminescence based microbial method: the effect of milk composition and assay performance in relation to an immunoassay and a microbial inhibition assay" J. of Food Protection vol. 63, No. 7, 2000 pp. 953-957.
Orth, P. et al. "Structural basis of gene regulation by the tetracyucline inducible Tet repressor-operator system" Nature Structural Biology vol. 7, No. 3, Mar. 2000, pp. 215-219.

Klock et al., "Heterologous Repressor-Operator Recognition Among Four Classes of Tetracycline Resistance Determinants", Journal of Bacteriology 1985; 161: 326-332.
Otwinowski et al., "Crystal structure of *trp* repressor/operator complex at atomic resolution", Nature 1988; 335: 321-329.
Weickert et al., "A Family of Bacterial Regulators Homologous to Gal and Lac Repressors", The Journal of Biological Chemistry 1992; 267: 15869-15874.
Hillen et al., "Mechanisms Underlying Expression of TN*10* Encoded Tetracycline Resistance", Annual Review of Microbiology 1994; 48: 345-369.
Hinrichs et al., "Structure of the Tet Repressor-Tetracycline Complex and Regulation of Antiobiotic Resistance", Science 1994; 264: 418-420.
Phillips et al., "Electrostatic activation of *Escherichia coli* methionine repressor", Structure 1994; 2: 309-316.
Schumacher et al., "Crystal Structure of LacI Member, PurR, Bound to DNA: Minor Groove Binding by α Helices", Science 1994; 266:763-770.
Kisker et al., "The Complex Formed Between Tet Repressor and Tetracycline-Mg$^{2+}$ Reveals Mechanism of Antiobiotic Resistance", Journal of Molecular Biology 1995; 247: 260-280.
Schumacher et al., "Mechanism of Corepressor-Mediated Specific DNA Binding by the Purine Repressor", Cell 1995; 83: 147-155.
Jacobs et al., "Cytosolic Intermediates for Cell Wall Biosynthesis and Degradation Control Inducible β-Lactam Resistance in Gram-Negative Bacteria", Cell 1997; 88: 823-832.
Soisson et al., "Structural Basis for Ligand-Regulated Oligomerization of AraC", Science 1997; 276: 421-425.
Bovee et al., "Validation and use of the CALUX-bioassay for the determination of dioxins and PCBs in bovine milk", Food Additives and Contaminants 1998; 15: 863-875.
Baron et al., "Tet Repressor-Based System for Regulated Gene Expression in Eukaryotic Cells: Principals and Advances", Methods in Enzymology 2000; 327: 401-421.
Kurittu et al., "Qualitative Detection of Tetracycline Residues in Milk with a Luminescence-Based Microbial Method: The Effect of Milk Composition and Assay Performance in Relation to an Immunoassay and a Microbial Inhibition Assay", Journal of Food Protection 2000; 63: 953-957.
Matthews et al., "Relieving repression", Nature Structural Biology 2000; 7: 184-187.
Orth et al., "Structural basis of gene regulation by the tetracycline inducible Tet repressor-operator system", Nature Structural Biology 2000; 7: 215-219.

(Continued)

*Primary Examiner* — James S Ketter
(74) *Attorney, Agent, or Firm* — Merchant & Gould P.C.

(57) ABSTRACT

The invention concerns a kit for detecting and/or quantifying a ligant (C), present in an analysis sample, by a receptor (A), characterized in that it comprises the following reagents: a single-stranded or double-stranded nucleotide sequence (B), and said receptor (A) consisting of a monomeric or multimeric proteinic entity including at least a first recognition site specific for said ligand (C) and a second recognition site specific for said nucleotide sequence (B); said ligand (C) being capable of positively or negatively modulating fixing of the receptor (A) by its specific recognition site on the nucleotide sequence (B).

26 Claims, 5 Drawing Sheets

OTHER PUBLICATIONS

Namwat et al., "Identification of the *varR* Gene as a Transriptional Regulator of Virginiamycin S Resistance in *Streptomyces virginiae*", Journal of Bacteriology 2001; 183: 2025-2031.

Stebbins et al., "Tetracycline-inducible systems for *Drosophila*", Proceedings of the National Academy of Sciences 2001; 98: 10775-10780.

Millipore Corporation, "Developing Immunochromatographic Test Strips—Rapid Lateral Flow Test Strips—Considerations for Product Development," Bedford, MA (2002): 1-38.

Hillen et al., "Purification of the TET repressor and TET operator from the transposon Tn10 and characterization of their ineraction," *The Journal of Biological Chemistry* (1982) 257 (11): 6605-6613.

Hillen et al., "Control of expression of the Tn10-encloded tetracycline resistance operon. II.Interaction of RNA polymerase and TET repressor with the tet operon regulatory region," *J. Mol. Biol.* (1984) 172: 185-201.

Kaszycki et al., "Tet repressor—Tetracycline interaction," *Journal of Protein Chemistry* (1996) 15 (7): 607-619.

Murk et al., "Chemical-activated luciferase gene expression (CALUX): A novel in Vitro bioassay for Ah receptor active compounds in sediments and pore water," *Fundamental and Applied Toxicology* (1996) 33: 149-160.

Degenkolb et al., "Structural requirements of tetracycline-Tet repressor interaction: Determination of equilibrium binding constants for tetracycline analogs with the Tet repressor," *Antimicrobial Agents and Chemotherapy* (1991) 35 (8): 1591-1595

Kachab et al., "The development of an enzyme-linked immunosorbent assay (ELISA) for cephalexin," *Journal of Immunological Methods* (1992) 147: 33-41.

Hillen et al., "Control of expression of the Tn10-encoded tetracycline resistance genes," *J. Mol. Biol.* (1983) 169: 707-721.

Oliver, C., "Conjugation of colloidal gold to proteins," *Methods in Molecular Biology* (1999) 115: 331-334.

Hermanson, G., "Bioconjugate Techniques," *Academic Press* (1996).

Smith et al., "Preparation and application of insulin-gold complex," *Colloidal Gold Principles, Methods & Applications* (1991) vol. 3 Academic Press: 243-263.

Handley, D., "The development and application of colloidal gold as a microscopic probe," *Colloidal Gold Principles, Methods & Applications* (1989) vol. 1 Academic Press: 1-17.

Handley, D., "Methods for synthesis of colloidal gold," *Colloidal Gold Principles, Methods & Applications* (1989) vol. 1 Academic Press: 13-32.

Bendayan, M., "Protein A-gold and Protein G-gold postembedding immunoelectron microscopy," *Colloidal Gold Principles, Methods & Applications* (1989) vol. 1 Academic Press: 33-94.

* cited by examiner

SEQUENCE LISTING

```
<160> NUMBER OF SEQ ID NOS: 2

<210> SEQ ID NO 1
<211> LENGTH: 42
<212> TYPE: DNA
<213> ORGANISM: Artificial Sequence
<220> FEATURE:
<223> OTHER INFORMATION: Synthetic

<400> SEQUENCE: 1
tttttttttt taatgcggta gtttatcaca gttaattgct aa                42

<210> SEQ ID NO 2
<211> LENGTH: 31
<212> TYPE: DNA
<213> ORGANISM: Artificial Sequence
<220> FEATURE:
<223> OTHER INFORMATION: Synthetic

<400> SEQUENCE: 2
ttagcaatta actgtgataa actaccgcat t                            31
```

METHOD FOR PERFORMING IN VITRO DIAGNOSIS USING GENE REGULATION MECHANISMS AND CORRESPONDING DIAGNOSIS KIT

FIELD OF THE INVENTION

The present invention relates to a method using, partly or entirely in vitro, well-known elements of control mechanisms for the expression of genes, which would have as its principal field of application the recognition and measurement of quantities of specific molecules such as antibiotics.

The invention also relates to a diagnostic toolkit for carrying out the method.

SCIENTIFIC BACKGROUND

Natural genetic control systems are defined as mechanisms that are able to modify the expression of genes depending on the presence or absence of certain specific molecules in the cellular environment.

The expression of genes may be controlled during the phases of transcription, growth and translation of nucleic acids (FIG. 1).

Negative and positive control of transcription are distinguished. In the former case, a protein receptor, called a repressor, prevents the gene from being expressed by attaching to its operator and also prevents the RNA polymerase from starting the transcription on the promoter. This system is very common in bacteria (tetR, varR, lacI). In the latter case, an activator or transcription factor which attaches to the DNA is required for starting the transcription. This system is common in eukaryotes (e.g. hormonal receptors) but it is also found in bacteria, as is the case with the activator ampR that controls the transcription of β lactamase ampC in Gram-negative bacteria such as *Citrobacter freundei* (Jacobs et al., Cell, Vol. 88 (1997), pp. 823-832) or purR (Schumacher et al., Cell, Vol. 83 (1995), pp. 147-155). In a similar fashion, the translation may also be controlled by the attachment of a repressor to the mRNA which prevents the ribosome from starting the translation into proteins. In eukaryotes, the growth of mRNA may additionally be controlled during the modification, splicing, transfer or stable phases.

Regulators are protein units that may be in 2 states: either in an active state (ATR) in which they may, by attaching to DNA or mRNA, control the expression of genes in a positive (+) or negative (−) manner and thus control the synthesis of proteins, or in an inactive state (ITR) in which they can no longer attach to a particular nucleotide sequence. Activation is normally due to allosteric transition by a repressor as a result of the presence or absence of a binding agent with a strong affinity at a specific site on the regulator. This is the case with bacterial regulators belonging to the lacI family (Weickert and Adhya, J. Biol. Chem., Vol. 267 (1992) pp. 15869-74) or with hormonal receptors in eukaryotes. Other biochemical phenomena such as oxidation, phosphorylation or glycosylation may also throw light on these regulators.

In this case where the mechanism is attached by a binding agent, regulators have two attachment sites:
- one is an attachment site on the DNA, often characterised by an exposed helix β turn β helix α (HTH) motif, characteristic of proteins linked to DNA;
- the other is an attachment site on the binding agent.

The presence of the binding agent, called an effector, on the regulator normally induces a modification of the shape of the latter so as to permit (or on the contrary to prevent) the attachment of this regulator to a specific nucleotide sequence. These effectors thus work as inducers or co-repressors. These most common configurations are shown in FIGS. 2A and 2B.

This is the case with purine, a co-repressor required for the attachment of the dimeric repressor purR which belongs to the lacI family of bacterial transcriptional regulators, to the purF operator (Schumacher et al., Cell, Vol. 83 (1995), pp. 147-155; Schumacher et al., Science, Vol. 266 (1994), pp. 763-770) or with L-tryptophan, a co-repressor of the trp dimer (Otwinowski et al., Nature, Vol. 335 (1988), pp. 321-329).

The majority of the other bacterial regulators of the lacI family, with the exception of purR, suppress a catabolic, non-biosynthetic reaction, the affinity of the regulators for the operator being greater in the absence of the binding agent on the repressor. Thus tetR and varR are dimers that also belong to the lacI family, which intervene in the mechanisms of bacterial resistance to tetracycline and virginiamycin antibiotics respectively. These repressors, which moreover are highly homologous in their sequences, may attach to the operators "tet" and "var" only in the absence of their respective binding agents, tetracycline or derivatives and virginiamycin S considered as inducing effectors (Hillen et al., Ann. Rev. Microbiol., Vol. 48 (1994), p. 345; Namwat et al., J.Bac., Vol. 183 (March 2001), pp. 2025-2031).

In the presence of an attached inducer, the regulators "release" the operator and the suppression is immediately removed. One may observe the synthesis of tetA and varS, transfer molecules in the membrane that catalyse the transfer of antibiotics out of the cell. This system requires very fine control since it controls the toxicity of the transfer molecule which will at the same time prevent the antibiotic from reaching its target (the ribosome) but it may also release other non-specific ions outside the cell, which is also lethal to the cell. TetR must therefore strongly suppress tetA until a low level of tetracycline (Tc) is present.

As for tetR, its three-dimensional structure is known in the presence of Tc as well as in the presence of the operator (Hinrichs et al., Science, Vol. 264 (1994), pp. 418-420, Kisker et al., J. Mol. Biol., Vol. 247 (1995), pp. 260-280; Orth et al., Nature Structural Biol., Vol. 7, (2000), pp. 215-219). This allows the better understanding of the molecular machinery. A precise orientation of a lateral chain of the terminal amino acids is required so as to allow high-affinity contact between the operator segment of the DNA and the regulator. When the tetracycline is attached, the distance centre-to-centre between the two HTH motifs of the dimer of tetR is increased by 5 and this slight structural modification is sufficient to break the high-affinity contact with the operator. Studies in vitro show that the affinity of tetR for the operator in the absence of Tc is $10^{12}$ to $10^{13}$ $M^{-1}$ and it falls by a factor of $-10^9$ in the presence of Tc. TetR forms the most efficient inducible transcription control system known to date (Orth et al., Nature Structural Biol., Vol. 7 (2000), pp. 215-219).

In addition, it should be noted with regard to homology of sequence, six classes (A, B, C, D, E and G) of tetR are known among Gram-negative bacteria. The genes that code for these receptors are plasmids or they are transferred by transposons and they can all be induced at nanomolar concentrations of tetracycline. The proteins share 29% of identical amino acids between the different classes, which suggests similar 3D structures (Hillen et al., Annu. Rev. Microbiol., Vol. 48 (1994), pp. 345-332; Klock et al., J. Bac., Vol 161 (1985), pp. 326-332).

As for varR, the affinity parameters in the presence and absence of the inducer are not yet known but it is probable that they are of a similar scale. The affinity of the antibiotic for its target, the 50S ribosome, being similar, a large difference between suppression and induction of the membrane transfer molecule is also vital to the cell.

Other less vital repressors such as lacI show a loss of activity of only $10^5$ in the presence of the inducer (Matthews et al., Nature Structural Biol., Vol. 7 (2000), pp. 184-187).

Here again one should note that there are exceptions since ampR attached to the operator may activate transcription in vitro in the absence of a binding agent or in the presence of the binding agent anhydro-Mur Nac tripeptide. On the other hand, in the presence of another binding agent of ampR, UDP-Mur-Nac pentapeptide, transcription is inhibited (Jacobs et al., Cell, Vol. 88 (1997), pp. 823-832). AraC attaches to the DNA in the presence and the absence of the binding agent (L-arabinose) but transcription is only started in the presence of the binding agent following a DNA "loop" (Soisson et al., Science, Vol. 276 (1997), pp. 421-425).

Still other repressors such as MetJ attach to the operator only in the presence of the positively-charged co-repressor (s-adenosylmethionine) which, rather than a change of configuration, induces an electrostatic effect in the regulator, which increases its affinity for DNA by more than 1,000 times (Phillips and Phillips, Structure, Vol. 2 (1994), pp. 309-316).

STATE OF THE ART

To date, no invention, that is to say no combination of technical methods, has shown the possibility or the feasibility of exploiting the combination of molecules, nor in particular only certain molecules, involved in the mechanisms of genetic control, for the development of diagnostic tools in vitro with the aim of detecting the presence and/or measuring the concentration of certain substances which may be present in a sample to be analysed.

The present invention does not claim to rely on any particular method of development of cells in culture in order to work and cannot concern applications in which it is the genetic control mechanism itself which is cloned and exploited in vivo in a strain of bacteria or a cellular lineage. In the latter very special case, cellular development or bacterial growth in a nutritive medium is in fact indispensable to allow the in vivo expression of the genetic control mechanism. Certain applications of this kind show the possibility, based on genetically recombinant cells, of creating means of measurement and of measuring concentrations of substances which may be present in a sample. This is in particular the case for the measurement of concentrations of dioxins known as Calux® (Chemical Activated LUciferase gene eXpression) described in the American patent No. U.S. Pat. No. 5,854,010 (Bioassay for detecting 2,3,7,8-tetrachlorodibenzo-para-dioxin and TCDD-like compounds and novel recombinant cell line useful therefor). This diagnostic kit works for the measurement of concentrations of dioxins and their derivatives (Murk et al., Fundam. Appl. Toxicol., Vol 33(1) (September 1996), pp. 149-60; Bovee et al., Food Addit. Contam., Vol. 15(8) (November-December 1998), pp. 863-75). According to this document, the inventors have created an expressive plasmid into which they have inserted the genetic elements that respond to dioxin in advance of the gene carrying the luciferase. The plasmid is transferred to the epithelial cells of mice. These are cell lineages that are used in a procedure for the quantitative analysis of the concentration of poly-aromatic hydrocarbon in a sample.

Another system known as "Tet-Lux" is based on an identical principle (Kuritti et al., J. Food Prot., Vol. 63(7) (July 2000), pp. 953-7). In this application, it is the control system for the resistance to tetracycline which is cloned in advance of a luciferase gene in the location of and instead of the gene for resistance to tetracycline. In the presence of tetracycline in the growth medium of the recombinant cells, the gene for luciferase can be expressed and with the help of luciferin, light is emitted. In the absence of tetracycline, the control system is inactive and no light is produced.

Document U.S. Pat. No. 6,133,027 describes compounds and methods for the inducible expression of a cytotoxic polypeptide for the eukaryotic host cell in which the polypeptide is expressed. The sequence of nucleotides that codes the said polypeptide is connected with a primer consisting of multiple copies of tetO, the attachment site of the tetracycline repressor tetR. The system of expression is cellular.

TetR-tetO makes up the most sensitive transcription control system known to date. The power of systems (tet) inducible with tetracycline has also permitted the development of a favoured method for transgenic research. They are often used as a tool for controlling particular target genes in eukaryotes (Stebbins et al., PNAS, Vol. 98(19) (2001), pp. 10775-80; Baron et al., Methods Enzymol. (2000), Vol. 327 pp. 401-421). The authors report that a low level of doxycycline added to the usual food of *drosophila* rapidly and efficiently induces the target transgenes in the adults, larvae and embryos.

The major disadvantage of a method which requires cellular development lies in the time required for the release of the measurable signal. Several multiplications of the cells and a wait of at least one hour are required before a readable signal is obtained. In certain cases, the sample may also contain elements which are liable to modify the growth of the recombinant cells in an unspecified manner and to cause errors or add to the noise in the final measurement. Moreover, these recombinant cells are sometimes unstable and may be very sensitive to various factors. In addition, their use in a test toolkit is not suited to simple and practical handling, especially when tests have to be carried out in conditions in the field. Moreover, these kinds of test often require the intervention of an expert or a qualified operator in order to carry out the analysis. Lastly, the reagents and instruments which measure the light emitted are very expensive.

AIMS OF THE INVENTION

The present invention aims to provide a new diagnostic method which does not have the disadvantages and difficulties of the present state of the technology mentioned.

In particular, the invention aims to propose the use in part or entirely of familiar elements for controlling the expression of genes for the development of methods and/or substances, usable in vitro, whose main area of application would be the recognition and measurement of quantities of molecules.

A supplementary aim of the invention is to provide a quick diagnostic test of specific molecules.

A supplementary aim of the invention is to provide a method and a diagnostic toolkit in vitro for the detection and measurement of the concentration of antibiotics such as tetracyclines and virginiamycins.

MAIN CHARACTERISTIC ELEMENTS OF THE INVENTION

A first objective of this invention is to propose a toolkit for the detection and/or measurement of the level of a binding agent, located in an analysis sample, by means of a receptor. The binding agent is likely to be present in a sample of biological material, normally being present in solution for practical reasons. The toolkit contains the following reagents:

a single or double-strand nucleotide sequence, and said receptor consisting of a monomer or polymer protein part containing at least a first specific recognition site for said binding agent and a second specific recognition site for said nucleotide sequence.

The special feature of the binding agent is its capacity to modify positively or negatively the attachment of the receptor to its specific recognition site in the nucleotide sequence.

As an advantage, the binding agent is an antibiotic, preferably belonging to the family of tetracyclines or virginiamycins, or a related substance. Hence one chooses as a receptor a tetracycline repressor (tetR) isolated from any of the known classes, that is A, B, C, D E and G, or virginiamycin (varR), which is used for the measurement of concentrations of tetracyclines and virginiamycins respectively.

One particularly advantageous feature of the invention is that it includes a means of carrying out the measurement of the concentration of the antibiotic in a very short time, preferably less than 15 minutes, this being for concentrations approaching the maximum residue limits permitted.

The receptor may also be, according to the invention, a nuclear receptor of the family of eukaryotic transcription regulators, a receptor of the family of "orphan receptors", their binding agents being unknown to date, or even a mutant of the natural tetracycline or virginiamycin receptors, nuclear receptors or orphan receptors.

According to the invention, the nucleotide sequence is a double-strand fragment of a specific sequence of the operator segments of the genes tetA and tetR for the recognition of tetracyclines or varA and varR for the recognition of virginiamycins, said fragment preferably being located at the end 3' of an element made of a biotin and of a single-strand poly-T chain.

According to a first preferred embodiment of the invention, the nucleotide sequence is fixed, directly or indirectly, on a solid support, the receptor possibly being marked by at least one molecule.

According to a second preferred embodiment of the invention, the receptor is fixed, directly or indirectly, on a solid support, preferably by means of a specific antibody and an A-protein, the nucleotide sequence possibly being marked by at least one molecule.

As an advantage, the receptor or the nucleotide sequence, as applicable, is marked, directly or indirectly, by means of an antibody or a biotin. The antibody and the biotin respectively may be marked by the intermediary of an A-protein and by a molecule that fixes the biotin. This direct or indirect marking is preferably made by means of coloured particles such as particles of colloidal gold, or by means of an enzyme such as peroxidase.

A surprising feature of the invention is that no marked element is required for detection, the mere presence or absence of the complex of receptor and nucleotide fragment being detectable by a physicochemical method of the Surface Plasmon Resonance type or mass spectrometry.

As an even greater advantage, the nucleotide fragment, linked to a biotin, is associated with a protein which fixes the biotin, preferably avidin, streptavidin, neutravidin or an antibiotin antibody, so as to form a complex which is deposited on a membrane of nitrocellulose, defining a first point of detection for the receptor and the nitrocellulose membrane bears a second detection point which is able to recover, entirely or in part, the excess of reagents that is not fixed at the first detection point.

The second detection point preferably contains gamma-globulin, A-protein or A-antiprotein.

As a further advantage, the toolkit in the invention contains a means of quantifying, after detection, the signals obtained at the two detection points, either by visual inspection, or by optical measurement (reflectivity, absorption, transmission, fluorescence, digital camera, chemoluminescence), or by Surface Plasmon Resonance, or by mass spectrometry.

According to one feature of the invention, the receptor bears a third specific recognition site independent of the receptor's recognition sites for the nucleotide sequence and the binding agent.

As an advantage, the receptor's third specific recognition site is a recognition site for another protein unit, preferably an antibody or a specific fragment of antibody, or an attachment site for a metallic ion. The other protein unit that interacts with the third recognition site is marked, preferably by means of an A-protein associated with particles of colloidal gold.

The invention may be exploited in an extremely practical fashion when the receptor for the nucleotide sequence and/or the antibody and/or a fragment of the latter is marked by at least one molecule allowing detection by a procedure such as immunoprecipitation, immunochromatography, ELISA or RIA-type detection, the formation of a coloured precipitate resulting from an enzymatic reaction, etc.

Still regarding the practical aspect of the invention, said reagents are preferably contained in a lyophilised flask and on a unit of an immunochromatographic strip type.

Alternatively, the toolkit may also be without a flask; said reagents are then directly in contact with the inside of the strip unit on a membrane near its end which can be brought into contact with an analysis liquid.

A second aim of this invention concerns a method of detecting and/or of measuring the quantity of a binding agent present in a preferably biological sample, carried out by means of the toolkit described above and characterised in that:

said sample is brought into contact with the toolkit and by the fact that the presence of the binding agent is detected or its concentration measured in said sample by immunochromatography or by enzymatic concentration measurement, preferably of the ELISA type, by SPR or by mass spectrometry.

This method has the advantage that the biological sample can be brought directly into contact with the toolkit's reagents without having to be purified in advance. In addition, there is no restriction on the nature of the biological sample used, the latter being of meat, fish, blood, serum, a bodily fluid, urine, tears, saliva, milk, honey, water, animal feedstuffs or any other food preparation or culture or fermentation liquids, or preparations or derivatives of these substances.

Lastly, although the invention has been described and illustrated in its preferred and most developed embodiments, various variants appear to be possible and they also fall equally well within the framework and spirit of this invention. In particular, the last claim covers a large range of variants relating to a method of detection and/or quantification of a binding agent molecule, using in vitro, entirely or in part, a variety of elements, preferably methods, mechanisms and/or substances, known from natural control mechanisms for the expression of genes in vivo. The method is distinguished in general by the fact that one uses a linking monomeric or polymeric protein unit called a receptor or regulator which originates in said natural genetic control mechanisms, bearing several different specific recognition sites, the state of reactivity of each of said sites relative to its own binding agent being able to modify the reactivity of at least one other recognition site for said receptor.

Said reactivity of at least one recognition site of the protein receptor for a nucleotide sequence for instance of the genetic promoter/operator type, may preferably be modified by an adjustment of the centre-to-centre distance between two HTH motifs of a dimer belonging to said receptor.

GENETIC MECHANISMS AT THE BASIS OF THE INVENTION

Figure 1:
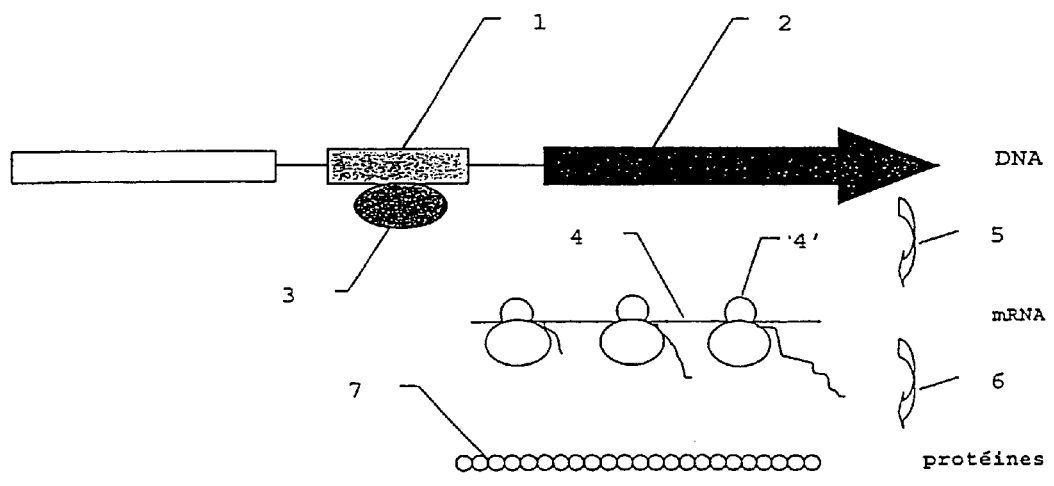
FIG. 1, which has already been mentioned above, shows in a very schematic fashion the control mechanism for genetic transcription as it occurs in vivo.

FIG. 1 shows the classic control scheme for the transcription of a structural gene 2. The transcription 5 of DNA into mRNA is initiated by the attachment of the polymerase RNA 3 to the control region at the head of the (promoter/operator) gene 1. The translation 6 of mRNA 4 into proteins 7 is then carried out in the ribosomes 4'.

Figure 2A:
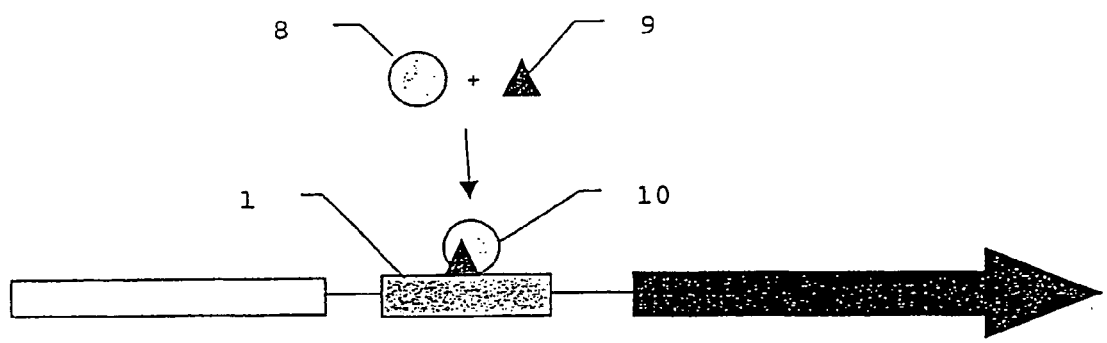
FIGS. 2A and 2B, which have been mentioned above, show the activation and inactivation mechanisms respectively of the regulator in the presence of a binding agent.

The activation of the regulator 8 in the presence of an inducer binding agent 9, is shown in FIG. 2A. When the inactive transcription regulator (ITR) 8 attaches to the promoter 1, after fixing the binding agent 9, so as to create an active transcription regulator (ATR) 10, there is activation or non-activation of the transcription of the gene depending on whether the ATR is a transcription activator or repressor respectively.

Figure 2B:
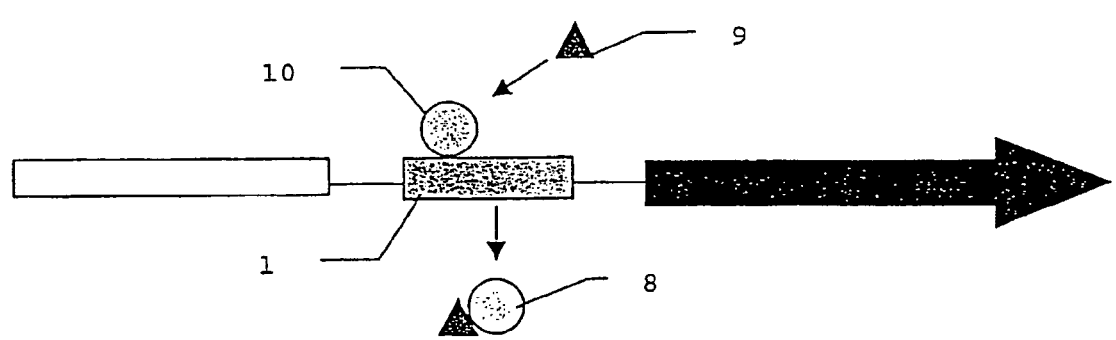

The non-activation of the regulator 8 in the presence of a co-repressor binding agent 9 is shown in FIG. 2B. When the ATR 10 is attached to the promoter 1, there is activation or non-activation of the transcription depending on whether the ATR is a transcription activator or repressor respectively. The attachment of the binding agent 9 to the ATR 10 causes it to be detached from the promoter 1 with the ITR 8, 9, which induces the suppression or activation of the gene respectively.

DETAILED DESCRIPTION OF A PREFERRED EMBODIMENT OF THE INVENTION

The present invention is based on the use of a monomeric or polymeric protein unit, normally originating in known mechanisms of genetic control, which bears several distinct recognition sites and in which the reactive state of a site to its own binding agent may modify the reactivity of another recognition site in this same protein unit. In the particular case of the invention, we are concerned with the recognition of a fragment of nucleic acid and a binding agent, the attachment of the binding agent being able to negatively affect (i.e. prevent) the recognition of the DNA sequence by the protein unit.

In other words, the invention is based on the use in in vitro diagnostics techniques on complexes of the "DNA sequence-regulator-binding agent" type for the detection of substances related to or derived from the molecule of the binding agent.

This invention has the advantage of not having to resort to the expression of a biological system in vivo, and does not require the use of particular cell lineages.

As such this invention exploits the known characteristics of genetic control systems but in a totally different technology and one much better adapted to quick testing. In fact the biological molecules are used in vitro without having to resort to any cellular infrastructure or development or to any expression of a biological system in vivo. It is the three key elements, being nucleic acid/receptor/any binding agent, originating in the control systems, which, placed in an environment external to that of any cellular viability are capable of expressing their functionality outside the cellular context. In one particular application which concerns the concentration of tetracyclines, the basic reagents, provided in a single mixture, have been directly measured in the analysis sample and the response was obtained in 5 minutes.

Figure 3:
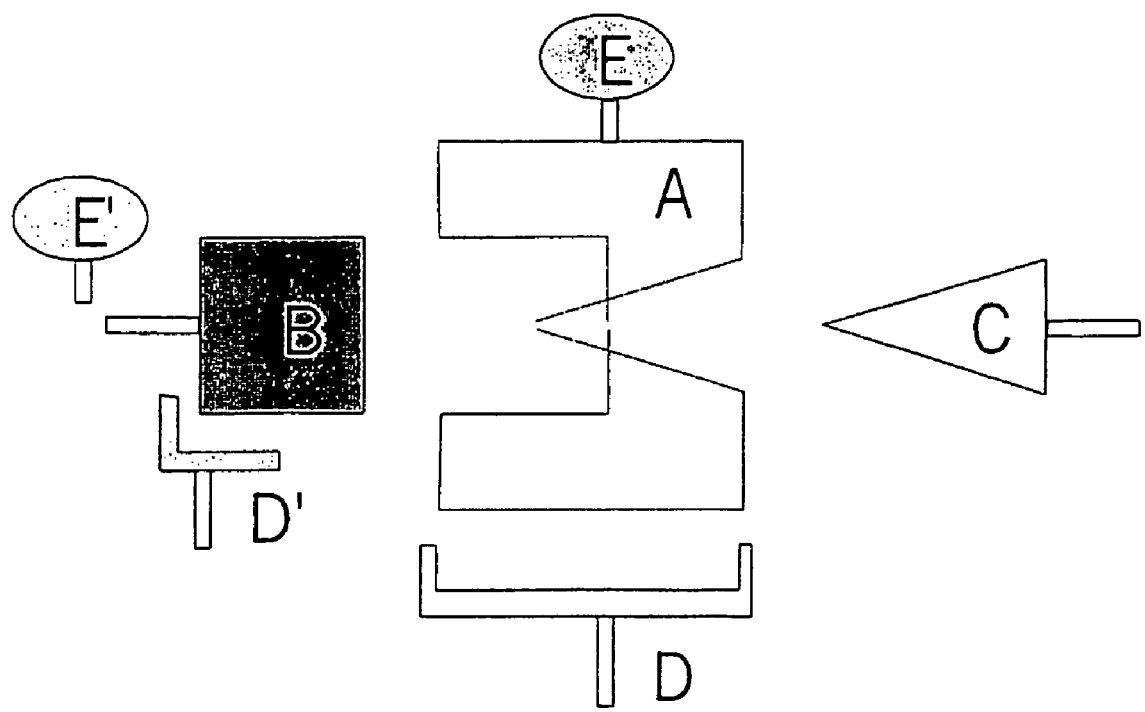
FIG. 3 shows the simplified schematic transposition of the mechanisms shown in FIGS. 2A and 2B as in this invention and its various preferred embodiments.

FIG. 3 simplifies the description of the invention by showing the various approaches proposed in this patent application. FIG. 3 shows schematically in the simplest expression both the set of key elements that support the invention and the set of indispensable elements so as to then detail the particular embodiments of the invention.

The key elements are three in number:
firstly a protein unit capable of recognising a connecting molecule and a fragment of nucleic acid,
secondly a connecting molecule (binding agent) capable in its turn of recognising the protein unit concerned and
thirdly a fragment of nucleic acid, DNA or mRNA, that the protein unit is also capable of recognising.

There are thus two distinct recognition sites borne by a protein unit, which unit may be in monomeric or polymeric form, and preferably polymeric.

In FIG. 3, one therefore distinguishes a protein unit A capable of specifically recognising a nucleic acid sequence B and attaching to it either only in the presence or only in the absence of the binding agent C. When C attaches to A, the complex AC can then no longer attach to B or A is even detached from B. In the opposite case (not shown), it is only the complex AC which allows A to connect to B and in the absence of C, A detaches from B.

A fragment B of nucleic acid may thus be recognised by A, either in one case only in the absence of C, or in the other case only in the presence of C.

A binding agent C specific to A may attach to A irrespective of the state of interaction of A and B. Its attachment to A prevents A from fixing B or forces the AB complex previously formed to break up or, in the opposite case, it is the formation of the AC complex that allows AC to attach to B so as to form the complex ACB. A lowering of the concentration of C forces the complex ACB to break up completely.

One may also have another recognition site D, external to and independent of A's recognition site for B and C. This may be a recognition site for another protein unit, mormally an antibody or a fragment of antibody, capable of attaching to A independently of the attachment of B or C to A. It could also be for instance an attachment site for a metallic ion or some other kind of protein. In a similar fashion, there could be another recognition site D' for the DNA (B) that plays the same role as D but relative to B.

There can also be an artificial link E added to A, either by chemical bonding or for example by genetic or protein engineering. This link does not modify the functionality of A (relative to B, C or D). This link may serve as an anchor point for A to any other molecule to mark A or to fix A to a support, for instance. The artificial link E' plays the same role as E, but relative to B.

In a general sense, this invention applies to diagnostic techniques that normally require two principal elements, normally one detection element and one marking element. These two elements are sufficient to work through a whole set of possibilities which will in fine allow the description and the support of the argument presented in this invention.

According to this invention, each and every one of the elements described in FIG. 3 (A, B, C, D, D', E and E'), without exception, may or may not be either fixed and serve as a point of detection or be marked. Direct or indirect fixing to a support of any kind allows the possible total or partial recovery of the complex that is present, whatever the state of the complex formed. Direct or indirect marking by any molecule or particle or by any combination of molecules permits one to identify or to view directly or indirectly the possible form of the complex present, whatever the state of the complex formed, on the detection element. In one particular case, the detection and/or marking elements are not indispensable since it is the simple physical presence or absence of the complex formed which is detected by more sophisticated techniques such as physicochemical techniques of a mass spectrometry (MS) type or of a Surface Plasmon Resonance (SPR) type, for instance.

In general, if one of these elements is fixed so as to permit the possible recovery of the complex present, it will be another element that will possibly be modified to serve as a marker for the complex that is present and vice versa.

Marking may be achieved notably by means of coloured particles for detection in the context of an immunochromatography application, by means of a marker enzyme for detection in the context of an ELISA-type application, or it may be achieved by a fluorescent molecule for detection in the context of an application of detection of fluorescence. In the case where physicochemical methods would be used (for instance MS, SPR, etc.), external marking is not necessary since these methods are capable of detecting the presence or absence of molecular complexes.

In general, the fixing of any of the elements may be carried out on a support:
- of a natural or synthetic membrane type (nylon, PVDF, nitrocellulose, etc.),
- of a plastic surface type (polycarbonate, polystyrene, PVP, PVC, polypropylene, etc.)
- of a magnetic particle type, or latex particle type, of a type with a metal, glass, ceramic or silica surface, etc., whether this is directly or indirectly by the intermediary of polymer chains (e.g. dextran, PEO, . . . ) or even of any chemical "spacer".

EXAMPLES

The present invention is illustrated in three key examples in which one assumes that the receptor's binding agent is the molecule to be detected in the analysis sample. In this case in the examples, the binding agent is the tetracycline present in the analysis sample.

The first example demonstrates the measurement of the level of tetracycline in meat by an immunochromatographic technique. One variant of this example also works for this measurement in milk or any other product derived from milk, but also in fish, serum or any other body fluid, in blood, urine, tears or saliva. The technique described in this invention also works in an ELISA version or the receptor can be marked by means of an enzyme (alkaline phosphatase or peroxidase etc.), either directly or indirectly with the help of the biotin-avidin system.

The second example demonstrates the measurement of tetracycline levels in milk products by an ELISA technique. One variant of this example also works for the measurement in meat, fish, serum or any other body fluid, blood, tears, urine, saliva. The technique also works in an immunochromatographic version where the marking of the DNA is then done by the intermediary of an anti-biotin antibody or of an avidin or streptavidin or one of their derivatives, marked with colloidal gold.

The third example demonstrates that it is possible to detect the presence of tetracycline in solution by means of a technique of a physicochemical type, preferably the *Surface Plasmon Resonance* (SPR) technique, without having to resort to any marking. In fact in this case it is the presence or absence of the receptor-DNA complex which is directly revealed.

Example 1

This example demonstrates this invention in the case of measurement in vitro of the level of tetracycline in meat (immunochromatographic technique).
Basic Principle The fragment of DNA B is fixed and the receptor A is marked, either directly by a biotin E or indirectly by an antibody D and an A-protein conjugated with particles of colloidal gold. The tetracycline to be detected forms the binding agent C shown in FIG. 3. In this example, the technological tool used to reveal the tetracycline is an immunochromatographic test but a similar version using enzyme marking also works in ELISA. The example demonstrates a measurement of the level of tetracyclines in meat, but the measurement works in just the same manner if the sample is any other biological matrix.

The preparation of the required elements is described below.
1.1 The Receptor

TetR is a particularly interesting receptor for tetracycline (Tc). It is a homodimer consisting of 2 identical sub-units each of 27 kD. One feature is that it is specific to tetracycline. In fact, this protein receptor has the function in vivo of fixing the tetracycline present in the cytoplasm, which releases the tetracycline resistance mechanism. Another feature is that it has a very high affinity for tetracycline and its derivatives (Ka valent from $10^9$ to $100 \times 10^9$ $M^{-1}$). The complex formed also tends to be relatively stable ($t_{1/2} \geq 2$ hrs at 37° C.). The affinity of Tc for other macromolecules such as ribosomes, the cell targets of these antibiotics, is slightly weaker ($10^6$ $M^{-1}$).

TetR is a protein located in the cytoplasm of Gram-negative bacteria that are resistant to tetracycline. It is thus a homodimer (Hillen et al., J. Mol. Biol., 169 (1983), pp. 707-721) consisting of two identical sub-units, each having:
- a head for attachment to the operators of genes tetA and tetR arranged in tandem, the helix α -turn β-helix α (HTH) motif characteristic of proteins being associated with DNA being located in the N-terminal region of tetR;
- a cassette for attachment to the $(Mg-Tc)^+$ complex (Kaszycki et al., J. Prot. Chem., Vol. 15 (1996), pp. 607-619).

Only molecules of tetracycline combined with a divalent cation ($Mg^{2+}$) may attach to a dimer of tetR. A dimer of tetR attaches to 2 molecules of Tc with the same affinity (Degenkolb et al., A.A.C., Vol. 35 (1991), pp. 1591-1595).

The formation of the tetR-Tc complex is optimised between pH 7.5 and 12 and is reduced at pH<7.5. At pH 5, the repressor is inactive (Hillen et al., J. Biol. Chem., Vol. 257 (1982), pp. 6605-6613). The complex remains stable up to 50° C.

The tetR-Tc and tetR-DNA complexes have been crystallised and their three-dimensional structures are known at 2.5 resolution (Hinrichs et al., 1994; Kisker et al., 1995; Orth et al., 2000). A large amount of structural information is therefore known about these complexes.

In the absence of $(Mg-Tc)^+$ in tetR, the two HTH regions may attach to the DNA with a very high affinity estimated in vivo at about $10^{11}$ M$^{-1}$ (Orth et al., 2000). By contrast, in the presence of the complex $(Mg-Tc)^+$ in tetR, the centre-to-centre distance between the HTH motifs increases by ~5, which prevents the tetR dimer from attaching to the operator region of the DNA. The affinity of tetR for DNA is thus reduced by a factor of ~$10^9$.

TetR-tetO forms the most effective control system for inducible transcription known to date, which makes tetR a favoured receptor for tetracycline and tetO a potentially ideal anchoring nucleotide sequence for tetR (Orth et al., 2000; Matthews et al., Nature Struct. Biol., Vol. 7(3) (March 2000) pp. 184-187).

An identical control system has just been described for *Streptomyces* as a mechanism for resistance to virginiamycin, a varR dimer equivalent to tetR and which contains two HTH motifs capable of attaching to an operator in the absence of an antibiotic. By contrast, when virginiamycin attaches to varR, a change of configuration prevents the latter from attaching to DNA (Namwat et al., J. Bac., Vol. 183 (Mar. 2001), pp. 2025-2031).

1.1.1 Preparation of the tetR Receptor

In the example selected, the gene of the receptor of tetR of class C contained in the plasmid pSC101 of *E. Coli* C600 has been cloned (available from American Type Culture Collection, Rockville, Md., USA) using the techniques well known to the specialist. On the basis of the nucleotide sequence, two primers have been selected for amplification by PCR of the gene which has then been cloned in a pet12a-expression plasmid.

Viable HB101 cells containing the plasmid pT7po123, coding for the polymerase RNA of the coliphage T7, are transformed with the product of the bond of the PCR fragment obtained and the pet12a. The cells cultured in LB medium are induced at DO600$_{nm}$=0.8 by a change of temperature to 42° C. for three hours.

The strategy employed to obtain protein homogeneity consists of 4 stages which are respectively:
I) cellular breakdown by means of the Constant Basic System;
II) an ion exchanger of source type 1SQ PE 4.6/100 of 1.7 ml (Pharmacia),
III) a molecular screen sephacryl S100 (Pharmacia) and
IV) a HiTrap heparin (Pharmacia).

At the end of the purification stage, the 99% pure protein is then stored at a concentration of 21 µM in a buffer of 10 mM of potassium phosphate, pH 7.9, 7 mM of β-mercaptoethanol in the presence of glycerol 50% by volume and at °20° C.

1.1.2 Marking the Receptor 1.1.2.1 Marking with Biotinylation

The receptor that recognises the tetracycline, prepared above, is chemically modified on its surface by the addition of a biotin (vitamin H). A derivative, N-hydroxysuccinimide ester (available from Unisensor S.A.), has been used. In one particular case, the biotinylation is carried out on the derivative cystine by the use of a biotin maleimide available from Pierce Inc., USA).

The biotinylation is carried out in accordance with the method described in *Bioconjungate Techniques*, Hermanson, G. T. (1996), Academic Press, New York. The biotinylated receptor is then dialysed from its preservation buffer made of potassium phosphate 20 mM, pH 7.9 and β-mercaptoethanol 14 mM. After dialysis, the receptor is then stored in this same buffer diluted to half strength in the presence of glycerol 50% by volume.

The biotin can be revealed by an antibiotin antibody or by streptavidin or by neutravidin combined with coloured particles (colloidal gold, latex, cellulose) when an immunochromatographic version is used, or combined with an enzyme (HRP, PA, etc.) when an ELISA type version is used.

1.1.2.2 Marking by Means of an Anti-tetR Antibody

The preparation of the antibody is carried out according to the method described in Kachab, E. H. et al., The Journal of Immunological Methods, Vol. 147, no.1 (Jan. 1, 1992), p. 33-41.

The antibodies can be revealed either after their modification by direct combination with gold (Method Mol. Biol. Totowa, N.J. Vol. 115 (1999), pp. 331-334; Colloidal Gold Principles, Methods and Applications, M. A. Hayat, Academic Press) or by biotinylation and revelation by an antibiotin antibody or neutravidin combined by enzymatic means or with the help of coloured particles, or without modifying the antibody, simply revealing it by an anti rabbit antibody or with A-protein also marked enzymatically or with the help of coloured particles.

In the examples for meat and milk, one part of the unpurified serum obtained above is placed in the presence of one part of the tetR receptor obtained above in 1.1.1., 5 parts of the A-protein marked by means of the particles of colloidal gold of 40 nm and of one DO at 500 nm of 10 (available from Unisensor S.A., Liege, Belgium) and 10 parts of lyophilisation buffer (Tris 10 mM, pH 8, BSA 5 mg/ml, sucrose 10 g/l). This mixture is lyophilised for 20 hours.

In the example showing the measurement of the concentration based on samples of honey, one unpurified part of serum obtained above is placed in the presence of one part of tetR receptor obtained above in 1.1.1, 15 parts of A-protein marked by means of particles of colloidal gold of 40 nm and one DO at 500 nm of 10 (available from Unisensor S.A., Liege, Belgium) and 20 parts of lyophilisation buffer (Tris 10 mM, pH 8, BSA 5 mg/ml, sucrose 10 g/l). This mixture is lyophilised for 20 hours.

1.2 The Nucleic Acid

The dimer of tetR has 2 HTH motifs capable of attaching to a specific sequence of DNA, the operator region of the genes tetR and tetA.

In the operon for resistance to Tc in the transposon Tn10, the operator regions of the genes tetA and tetR that fix the receptor tetR have been located and their sequences are known (Hillen et al., 1984).

By aligning the sequences, it has also been possible to locate this sequence preserved in the operator tetA of the pSC101 and to synthesise an oligonucleotide of 31 base pairs surrounding this agreed region (teta-40) as well as another oligonucleotide of 31 base pairs of a complementary sequence to the first one (teta-30). The first oligonucleotide (teta-40) will also have a poly-T tail in 5' (10 T), which will remain a single strand during the pairing of the two oligonucleotides, as well as a biotin at this end 5'.

A synthetic oligonucleotide of 31 base pairs with a tetR attachment site on the tetA operator of pSC101, as well as its biotinylated complement in 5', have been synthesised (Eurogentec, Belgium).

```
Teta 40: 5'bioin-TTTTTTTTTTTAATGCGGTAGTTTATCACAGTTAATTGCTAA 3'    (SEQ ID NO:1)

Teta 30: 3' TTACGCCATCAAATAGTGTCAATTAACGATT 5'                   (SEQ ID NO:2)
```

1.2.1. Preparation of the Nucleic Acid

For hybridisation, the two complementary oligonucleotides are mixed in equal molar quantities ($2 \times 10^{-4}$ M) in NaCl of 0.5 M. The mixture is incubated for 5 minutes in boiling water, then slowly cooled in this bain marie to ambient temperature so as to reduce the pairings.

1.2.2 Fixing of the Fragment of Nucleic Acid

The Fragment of nucleic acid is fixed to the avidin by the end of one of the strands that contains a biotin. The avidin is a tetrameric glycoprotein isolated from egg-white. Each sub-unit has a molecular mass of 16.4 kD and fixes a molecule of biotin in a non-covalent manner with a particularly high affinity ($K_a = 10^{15}$ M$^{-1}$).

The two oligonucleotides teta30 and teta40-biotin, previously hybridised at $10^{-4}$ M in NaCl 0.5 M, are placed in the presence of avidin at 20 mg/ml in water in a ratio of 10/1 by volume. The product of the reaction is deposited on a nitrocellulose membrane by means of a deposition system marketed by BioDot Inc., USA.

1.3 Description of the Technique Used

The immunochromatographic technique is known and described in the literature (*Developing Immunochromatographic Test Strips*: A short guide, Millipore, Lit. No. TB500 printed in USA 11/96, 96-204). In the precise case of the present invention, the mixture obtained above (see Point 1.2.2) is deposited on a nitrocellulose membrane. It is known that proteins, and here in particular avidin, attach by dipolar interaction in an irreversible manner to the nitrocellulose support. Moreover, it is known that nucleic acids in the form of double strands do not react with this same support. In other words, the mixture of avidin-biotin-nucleic acid is an advantageous choice where the avidin serves as an anchor and the DNA remains free and accessible for recognition by a protein, as it happens in the present example the receptor tetR.

The nitrocellulose membrane is then brought into contact at the two ends by any absorbent paper. One finds on the nitrocellulose two detection points, one consisting of the mixture of avidin-biotin-DNA described in the previous point and the other, located after the first by reference to the direction of flow of the liquid, is a protein capable of being recognised by the A-protein. This protein is preferably a gammaglobulin. This forms the strip element used in Example 1.

Figure 4:
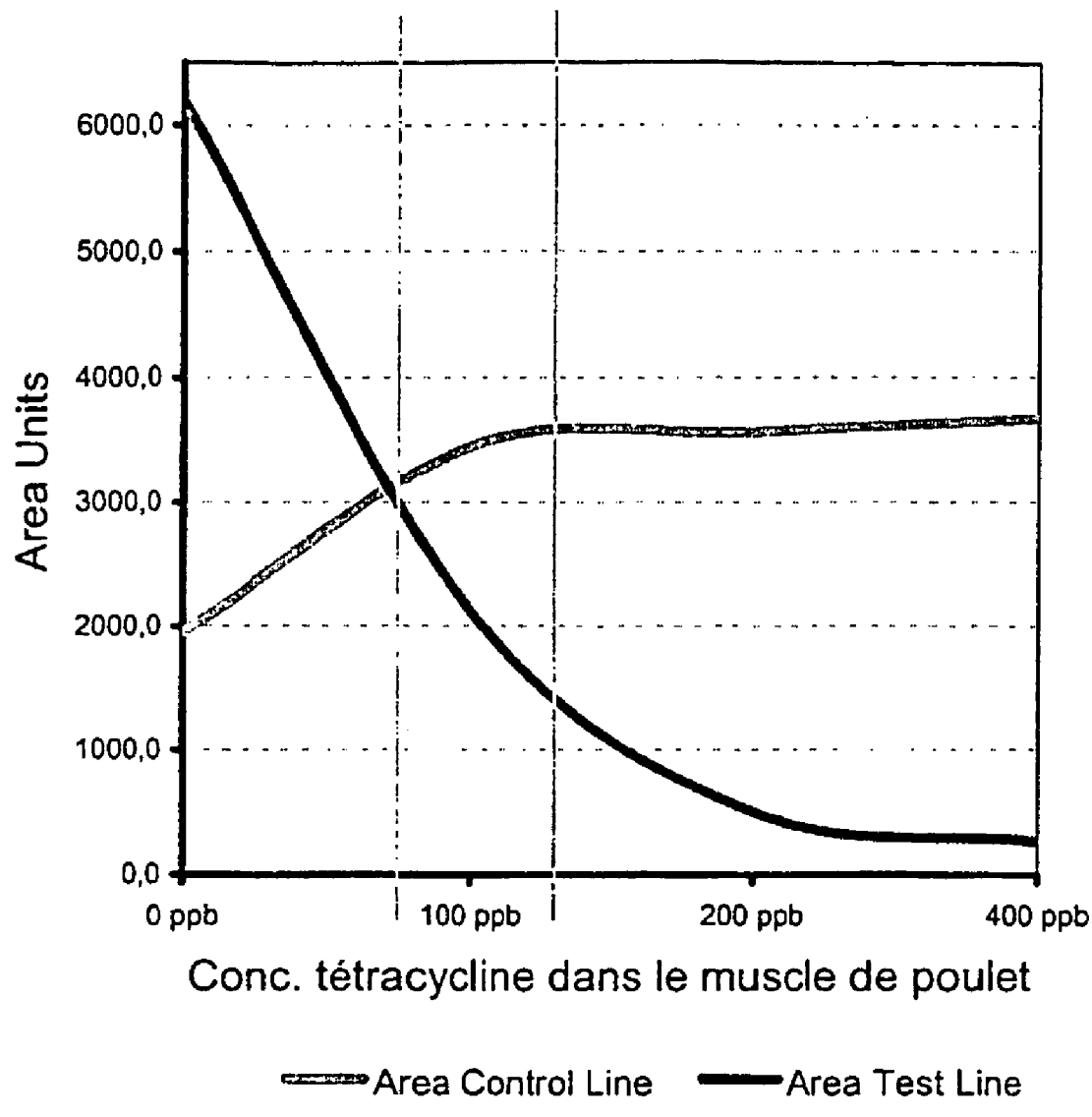
FIG. 4 shows a curve of the level of tetracyclines measured in the muscle of a chicken, as in the invention.

On this strip element, the first detection point forms the specific "test" zone (Test Line) for the presence or absence of tetracycline in the reaction medium and the second detection point is the "reference" zone (Control Line) capable of recovering the excess of the reagent not retained at the first detection point. The assessment of the quantity of tetracycline in the analysis sample is made by optical interpretation of the surface traces present at the detection points (see FIG. 4).

1.4 Measurement of the Level of Tetracyclines in Meat by Method 1

To 25 g of chicken muscle are added 75 ml of pH4 McIlvain buffer (1 litre of a monohydrate citric acid solution at a concentration of 21 g/l and 625 ml of a solution of anhydrous NaHPO4 at a concentration of 28.4 g/l, the pH being adjusted to a value of 4 by means of 0.1M NaOH) diluted to a quarter strength in water. The mixture is ground in a domestic mincer of the SEB Rondo 500 type for 2 minutes. The pulp is put into an Eppendorf so as to be centrifuged for 2 minutes at 6,000 rpm in a centrifuge of Eppendorf type. 200 µl of supernatant are then incubated in the presence of the lyophilisate prepared above (see Point 1.1.2.2). After two minutes of incubation at ambient temperature, ($\pm 20°$ C.), the analysis strip described above (in 1.3) is immersed in the solution. The final interpretation is carried out after 8 minutes of incubation by means of an optical strip reader available from 77-Elektronika (Budapest, Hungary). The results are summarised in FIG. 4. With this method, samples of chicken containing a small quantity of tetracycline of the order of 100 ppb may easily be detected in less than 15 minutes. This invention concerns the measurement of the level of tetracyclines at a value slightly below the Maximum Residue Limit (MRL) authorised in Europe. Below this level the test gives a negative signal and above this level the test gives a positive result.

Similar results have been obtained with muscle, kidney and liver from pork, chicken and beef but also from samples from fish and eggs. Where one wishes to observe the MRL applicable to kidney, liver and eggs, it is necessary to dilute the sample to a sixth ($6^{th}$), a third ($3^{rd}$) and a half ($\frac{1}{2}$) of the strength respectively in the McIlvain buffer described above, diluted to one eighth strength in water. For eggs it is not necessary to mince them.

It is remarkable to be able to confirm that this invention proposes, on the basis of a "solid" sample, in this instance a piece of meat, a method of quantifying antibiotics which can be carried out in a very short time (less than 15 minutes) and this being for concentrations close to or lower than the maximum residue limits (MRL's) permitted.

1.5 Measurement of the Level of Tetracyclines in Milk by Method 1

200 µl of milk are incubated in the presence of the lyophilised reagents and prepared as in Point 1.1.2.2. After two minutes of incubation at 37° C., the analysis strip described at 1.3 is immersed in the solution. The final interpretation is carried out after 8 minutes of incubation by means of an optical strip reader available from 77-Elektronika (Budapest, Hungary). The results are summarised in Table I. At 50 ppb, the "test" signal is below the "control" signal and the test gives a positive result.

TABLE I

| Tetracycline concentration in milk (ppb) | Test Line intensity | Control Line intensity |
| --- | --- | --- |
| 0 | 5,218 | 1,837 |
| 10 | 4,357 | 1,373 |
| 20 | 3,620 | 1,787 |
| 30 | 3,041 | 1,921 |
| 40 | 2,273 | 2,080 |
| 50 | 2,023 | 2,402 |
| 60 | 1,096 | 2,414 |
| 70 | 985 | 2,189 |
| 80 | 630 | 2,367 |
| 90 | 377 | 2,190 |
| 100 | 399 | 2,123 |

1.6 Measurement of the Level of Tetracyclines in Honey by Method 1

To 1 gram of honey are added 3 ml of dilution buffer (for 1 litre, 2.73 g of $Na_2HPO_4 \cdot 2H_2O$, 1.65 g of citric acid, 7 g of BSA and 2.5 g of Tween-20, pH 5) and the solutin is stirred vigorously so as to obtain a homogeneous solution. 200 µl of this dilution of the sample of honey are then incubated in the presence of the lyophilisate prepared above (see Point 1.1.2.2). After 10 minutes of incubation at ambient temperature (±20° C.), the analysis strip described above at 1.3 is immersed in the solution. The final interpretation is made with the naked eye, after 15 minutes of incubation at ambient temperature.

The following list summarises the tetracycline molecules that give a positive result at 25 ppb (which means that at 25 ppb, the "test" signal is lower than the "control" signal): chlortetracycline, demedocycline, doxycycline, methacycline, oxytetracycline, rolitetracycline and tetracycline.

Example 2

Example 2 Demonstrates this Invention for the Measurement of the Level of Tetracyclines in Milk (ELISA Technique)
Basic Principle In this example, using the terminology of FIG. 3, the receptor A is fixed by means of an antibody D and an A-protein and the DNA B is marked by means of a biotin E' and avidin peroxidase. In this example, the technological tool used to reveal the tetracycline is an ELISA test but in the case where the marking of the DNA would be done with the help of coloured particles, similar results may be obtained with immunochromatography. In Example 2, ELISA tubes or plates are used. Example 2 shows the measurement of the level of tetracyclines in milk, but the measurement works in exactly the same way if the sample is any other biological matrix.

The preparation of the required elements is described below.

2.1 The Receptor

The tetR receptor is produced and purified according to the method described at Point 1.1.1.

2.1.1 Preparation of the ELISA Support for the Recovery of the Receptor

1 μg of A-protein present in 100 μl of "coating" buffer (carbonate buffer 0.05 M pH 9.6) is deposited in each well of a microplate available from Nunc, Maxisorp F8 (ref.: 468667A) and incubated for one night at 4° C. The supernatant is aspirated the next day.

The wells are saturated for 30 minutes at ambient temperature with 200 μl of buffer of phosphate 0.01 M pH 7.4 BSA 0.5%, after which the supernatant is aspirated and the wells are washed with NaCl 0.15 M Tween 0.5%.

Lastly, 200 μl of buffer of phosphate 0.01 M pH 7.4 saccharose 1% are added and incubated for 30 minutes at ambient temperature. The wells are then washed and dried with compressed air and stored in a desiccator at 4° C. away from humidity.

2.2 Preparation of DNA Marked with Peroxidase.

We are dealing with the same preparation described in the above example at Point 1.2.1 which is placed in the presence of avidin peroxidase available from Pierce Inc. (Immunopure Avidin-Horseradish Peroxidase Conjugated ref. no. 21123). The reactive mixture described below reveals 10 picomoles of DNAds-biotin per 0.61 picomoles of avidin peroxidase.

2.3 Preparation of the Reactive Mixture

The reactive mixture is prepared in the following manner: 1 ml of solution contains:

I) 4.76 μl of tetR receptor 21 μM prepared as above (in buffer of phosphate 10 mM, pH 7.9, β-mercaptoethanol 7 mM, glycerol 50% by volume);

II) 2 μl of a solution of serum consisting of: 100 μl of serum prepared as in 1.1.2.2, 900 μl of buffer of phosphate 10 mM, pH 7 and 1 ml of glycerol;

III) 1 μl of biotinylated DNA as described in 1.2 ($10^{-4}$ M in NaCl 0.5 M);

IV) 2 μl of a solution of HRP avidin consisting of 100 μl of HRP avidin 1 mg/ml, 900 μl of buffer of phosphate 10 mM, pH 7 and 1 ml of glycerol;

V) 990.24 μl of buffer of phosphate 50 mM, pH 7.4, BSA 0.5%, $MgCl_2$ 10 mM.

2.4 Measurement of the Level of Tetracyclines in Milk by Method 2

50 μl of milk to be analysed are placed in the presence of 100 μl of the reactive mixture described above in a well pre-coated with A-protein (2.1.1). The mixture is incubated for 10 minutes at ambient temperature on a stirring table. The well is then washed 4 times with the washing solution (NaCl 0.15 M Tween 0.5%). Then 150 μl of tetramethylbenzydine/$H_2O_2$ 50/50 (KPL Inc., USA) are added to the well and the incubation is continued for 30 minute in the dark. The colouration reaction is stopped with 50 μl of $H_2SO_4$ 6 M and the reading is made by means of a spectrometer at 450 nm.

2.5 Measurement of the Level of Tetracyclines in Meat by Method 2

One variant of this example 2 shows the measurement of the level of tetracyclines in meat by an ELISA technique. In this instance, the sample is prepared as follows: 5 g of meat added to 15 ml of McIlvain buffer pH 4 (as described at Point 1.4) are ground in an Ultra-Turrax at 2,000 rpm for 30 seconds. 2 g (~2 ml) of pulp equivalent to 0.5 g of meat are centrifuged for 30 minutes at 13,000 rpm (15,000 g) at 4° C. The supernatant containing the extraction of the tetracyclines contained in 0.5 g of meat is deposited on a column of C18 Bond Eluent (Varian) 100 mg previously prepared with 1 ml of methanol followed by 1 ml of McIlvain buffer. After the column has been washed with 1 ml of $H_2O$ and dried by centrifuging for 5 minutes at 4,000 g (4° C.), the elution is carried out with 1 ml of methanol. After the evaporation of the methanol, the residue is collected in 50 μl of buffer of phosphate 0.01 M, pH 7.4, BSA 0.5%. At this stage, the sample is ready for the measurement as in the method described above in which the 50 μl of the sample extracted replaces the 50 μl of milk.

Figure 5:
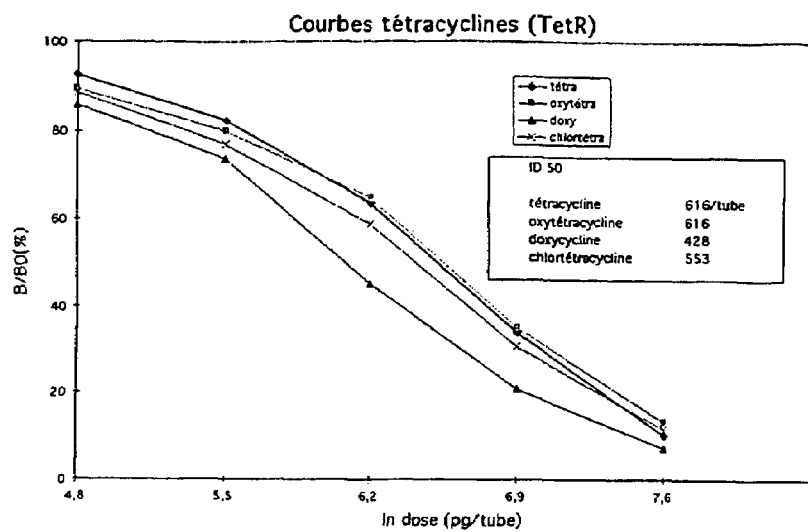
FIG. 5 shows graphically the level of four different tetracycline molecules measured by Method No. 2 of the invention.

FIG. 5 shows by way of an example the measurement of the level of four different tetracycline molecules by the same method. BO is the absorbency obtained in the absence of the antibiotic and B is the absorbency obtained in the presence of the antibiotic. ID 50 corresponds to the level of antibiotic required to obtain 50% saturation of the receptor.

Example 3

Example 3 shows this invention concerning the measurement of the level of tetracyclines without having to resort either to marking with coloured particles or to enzymatic marking. It is solely the presence of the complex formed that is detected. In this example, the recognition of the complex formed is carried out in an indirect manner by means of the Surface Plasmon Resonance technique (SPR technology, Biacore A.B., Uppsala, Sweden).

Basic Principle

In this example, using the terminology of FIG. 3, the fragment of DNA B (prepared in 1.2.1) is fixed to the Biacore streptavidin chip and the receptor A (prepared in 1.1.1) is used pure without having been marked. In the absence of tetracycline in the medium, the receptor-DNA complex is formed, which prevents the DNA bound to the receptor from attaching to the chip. In the presence of tetracycline, the free DNA always has the freedom to attach to the streptavidin and it is the attachment of the DNA to the chip which generates the increase in the signal.

Operational Method and Result

The chip is put in the reaction buffer which is composed of a solution of HEPES 75 mM, pH 7.5, NaCl 65 mM, MgCl$_2$ 15 mM and BSA 1 mg/ml.

A first solution labelled "FC1" of 323.1 µl is made up of 1.9 µl of DNA prepared as in 1.2.1, 10 µl of tetR 2.1 µM prepared as in 1.1.1 and 311 µl of reaction buffer.

A second solution labelled "FC2" of 323.1 µl is made up of 1.9 µl of DNA, 10 µl of tetR 2.1 µM, 4.2 µl of tetracycline 10 µM and 307 µl of reaction buffer.

Figure 6:
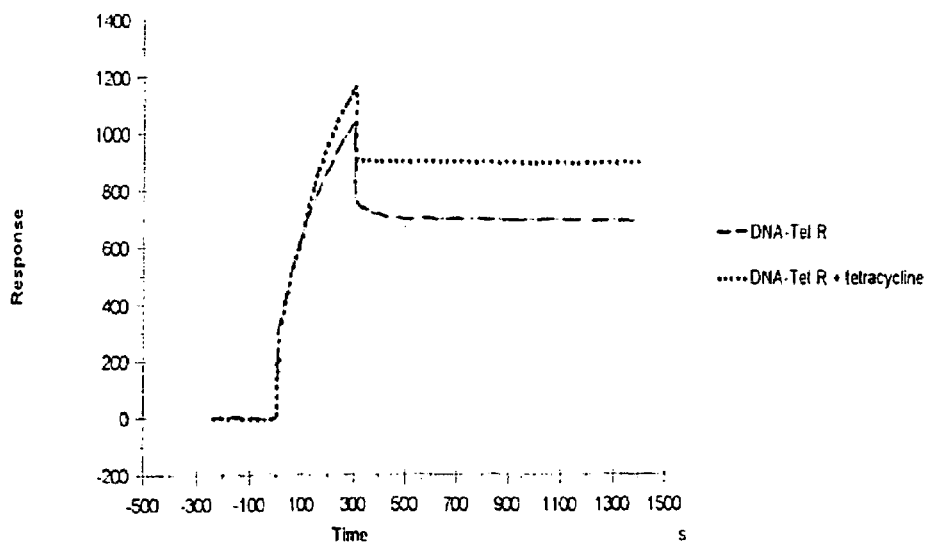
FIG. 6 shows graphically the results obtained by the SPR (Surface Plasmon Resonance) technique.

The above-mentioned solutions are incubated for 5 minutes at ambient temperature before being injected into the two respective channels for 5 minutes at 10 µl/min. In this experiment, it is shown in FIG. 6 that a concentration equivalent to 60 ppb of tetracycline, present in the analysis solution, does not permit the formation of the receptor-DNA complex, leaving the DNA free and able to attach to the streptavidin fixed to the chip. In the case of the FC1, that is in the absence of tetracycline, the receptor forms a complex with the DNA, preventing the latter from attaching to the streptavidin fixed to the chip. These results are a little unexpected as they are different to those observed in examples 1 and 2.

wherein binding of said antibiotic at the first recognition site is capable of modifying the binding of the operator nucleotide sequence at the second recognition site; and
   b) a solid support comprising the operator region nucleotide sequence, wherein the sequence is
     i) located at the 3' end of an element comprising biotin and a single-stranded chain of poly-T; and
     ii) directly or indirectly fixed to the solid support.

2. A toolkit for detecting the presence of a tetracycline or virginiamycin antibiotic comprising:
  a) a genetic repressor of a tetracycline or a virginiamycin antibiotic possessing
   i) at least a first recognition site specific to a tetracycline or virginiamycin antibiotic, and
   ii) a second recognition site specific to a nucleotide sequence comprising an operator region corresponding to the same gene expression system as said repressor,
  wherein the second recognition site is distinct from the first recognition site,
wherein binding of said antibiotic at the first recognition site is capable of modifying the binding of the operator nucleotide sequence at the second recognition site, wherein the operator nucleotide sequence is a reagent; and

---

---

The invention claimed is:

1. A toolkit for detecting the presence of a tetracycline or virginiamycin antibiotic comprising:
  a) a natural tetracycline genetic repressor TetR isolated from any of the classes of A to G TetR from gram-negative bacteria or a natural virginiamycin genetic repressor VarR possessing
   i) at least a first recognition site specific to a tetracycline antibiotic or virginiamycin antibiotic, and
   ii) a second recognition site specific to a double standard nucleotide sequence from operator regions of the tetA or tetR genes for recognition of tetracyclines or varA or varR genes for recognition of virginiamycins respectively,
  wherein the second recognition site is distinct from the first recognition site,
  b) a solid support comprising the genetic repressor, wherein the repressor is fixed to the solid support by means of a specific antibody and an A-protein, the operator region nucleotide sequence optionally being marked by at least a second molecule.

3. The toolkit according to claim 2, wherein the repressor is a natural tetracycline repressor TetR isolated from any of the classes A to G of TetR from gram-negative bacteria or a natural virginiamycin repressor VarR.

4. The toolkit according to claim 3, wherein the nucleotide sequence is a double stranded fragment of a specific sequence from operator regions of the tetA or tetR genes for recognition of tetracyclines or varA or varR genes for recognition of virginiamycins.

5. The toolkit according to claim 4, wherein said fragment is located at the 3' end of an element comprising biotin and a single-stranded chain of poly-T.

6. The toolkit according to claim 1, wherein the repressor is marked by at least a first molecule.

7. The toolkit according to claim 6, wherein the repressor is directly or indirectly marked by an antibody or biotin, said antibody or biotin being capable of being marked by an A-protein or by a molecule that fixes biotin,
wherein the repressor, antibody, or biotin is marked by colored particles or an enzyme.

8. The toolkit according to claim 2, wherein the operator region nucleotide sequence is directly or indirectly marked by an antibody or biotin, said antibody or biotin being capable of being marked by an A-protein or by a molecule that fixes biotin,
wherein the operator region nucleotide sequence, antibody, or biotin is marked by colored particles or an enzyme.

9. The toolkit according to claim 8 or claim 9, wherein the colored particles are colloidal gold.

10. The toolkit according to claim 8 or claim 9, wherein the enzyme is a peroxidase.

11. The toolkit according to claim 1 or claim 2, wherein a marked molecule is not necessary to detect a presence or absence of the repressor binding the operator region nucleotide sequence that is detectable by a physicochemical technique.

12. The toolkit according to claim 11, wherein the physicochemical technique is selected from the group consisting of surface plasmon resonance (SPR) and mass spectrometry.

13. The toolkit according to claim 1, wherein the operator region nucleotide sequence linked to biotin is associated with a protein that fixes biotin to form a complex that is deposited on a nitrocellulose membrane, thereby defining a first detection point for the repressor.

14. The toolkit according to claim 13, wherein the protein that fixes biotin is selected from the group consisting of avidin, streptavidin, neutravidin, and an anti-biotin antibody.

15. The toolkit according to claim 13 or claim 14, wherein the nitrocellulose membrane bears a second detection point capable of recovering, entirely or in part, excess reagents which are not fixed at the first detection point.

16. The toolkit according to claim 15, wherein said second detection point contains a component selected from the group consisting of a γ-globulin, an A-protein, and an anti-A-protein.

17. The toolkit according to claim 15, further comprising a means of quantifying signals obtained at the two said detection points by visual interpretation, optical measurement, Surface Plasmon Resonance, or mass spectrometry.

18. The toolkit according to claim 17, wherein the optical measurement is selected from the group consisting of reflectivity, absorption, transmission, fluorescence, digital camera, and chemoluminescence.

19. The toolkit according to claim 1 or claim 2, wherein the repressor further comprises a third specific recognition site, independent of the first and second recognition sites.

20. The toolkit according to claim 19, wherein the third specific recognition site specific for another protein unit or an attachment site for a metallic ion.

21. The toolkit according to claim 20, wherein said another protein unit is an antibody or a specific fragment of an antibody.

22. The toolkit according to claim 20, wherein said another protein unit interacts with the third recognition site and is marked by A-protein associated with particles of colloidal gold.

23. The toolkit according to claim 20, wherein at least one of a) the repressor or b) the antibody or antibody fragment is marked by at least one molecule that permits detection by at least one method chosen from the group consisting of immunoprecipitation, immunoebromatography, ELISA, or RIA-type detection and formation of a colored precipitate resulting from an enzymatic reaction.

24. The toolkit according to claim 1 or claim 2, wherein at least one of said repressor or nucleotide sequence is lyophilized in a flask.

25. The toolkit according to claim 1 or claim 2, wherein at least one of said repressor or nucleotide sequence is on an immunochromatic strip and directly in contact with the inside of said immunochromatographic strip on a membrane near its end that can come into contact with an analysis liquid.

26. The toolkit according to claim 25, wherein said immunochromatographic strip is formed by a linear support consisting of a nitrocellulose membrane linked to an absorbent paper bearing two detection points, a first detection point for recovery entirely or in part a nucleotide—repressor—antibiotic complex and a second detection point for recovering excess reagents not fixed at the first detection point.

\* \* \* \* \*